(12) United States Patent
Arai

(10) Patent No.: US 6,450,947 B1
(45) Date of Patent: Sep. 17, 2002

(54) ENDOSCOPIC TERMINAL PROCESSOR

(75) Inventor: Kaoru Arai, Omiya (JP)

(73) Assignee: Fuji Photo Optical Co., Ltd., Omiya (JP)

(*) Notice: Subject to any disclaimer, the term of this patent is extended or adjusted under 35 U.S.C. 154(b) by 0 days.

(21) Appl. No.: 09/397,097

(22) Filed: Sep. 16, 1999

(30) Foreign Application Priority Data

Sep. 18, 1998 (JP) .......................................... 10-265036

(51) Int. Cl.⁷ ................................................ A61B 1/64
(52) U.S. Cl. .......................... 600/109; 600/160; 340/65
(58) Field of Search ................................ 600/109, 160, 600/101, 110; 361/801, 818, 758, 750, 792, 802, 804, 741, 756, 748, 752; 340/65, 76

(56) References Cited

U.S. PATENT DOCUMENTS

| 4,574,332 A | * | 3/1986 | Calabro ....................... 361/784 |
| 4,868,716 A | | 9/1989 | Taylor et al. |
| 4,941,456 A | | 7/1990 | Wood et al. |
| 5,546,282 A | * | 8/1996 | Hill et al. .................... 361/801 |
| 5,847,923 A | * | 12/1998 | Lee ............................. 361/801 |

FOREIGN PATENT DOCUMENTS

| DE | 101 525 | 11/1973 |
| DE | 25 16 746 | 10/1976 |
| EP | 25 626 | 3/1981 |
| EP | 68 417 | 1/1983 |
| JP | 408106053 A | * | 4/1996 |

\* cited by examiner

Primary Examiner—John M. Mulcahy
(74) Attorney, Agent, or Firm—Oblon, Spivak, McClelland, Maier & Neustadt, P.C.

(57) ABSTRACT

An endoscopic terminal processor for an electronic endoscope, which accommodates within its casing an illumination light source along with a video signal processor for an electronic endoscope. A circuit board of the video signal processor is supported compactly in an upright position within the casing, and fixedly connected at one end to an inner surface of a side panel of the casing, and loosely supported at the other free end on a damper member adapted to restrict flapping movements of the circuit board about the fixed end and to permit movements in other directions to some extent to evade collisional impacts or shocks which might be transmitted from the casing.

4 Claims, 9 Drawing Sheets

ENDOSCOPIC TERMINAL PROCESSOR

BACKGROUND OF THE INVENTION

1. Field of the Art

This invention relates generally to electronic endoscopes which are in use in medical fields, and more particularly to an endoscopic terminal processor which contains within its casing an illumination light source along with a video signal processor for an electronic endoscope.

2. Prior Art

Electronic endoscopes which are currently in wide use for medical purposes are generally provided with an illumination window and an observation window side by side at the distal end of an insertion instrument to be inserted into a patient's body cavity, permitting observation of an intracavitary site of interest under illuminated conditions. An electronic endoscope differs from an optical endoscope in that the endoscopic observation system employs an electronic image sensor means such as CCD camera or the like for an image pickup to be fitted in the observation window. Therefore, in the case of an electronic endoscope, a signal cable from the image sensor means is passed through an insertion instrument along with an illumination light guide from the illumination window, and extended into a universal cable which is led out from a manipulating head assembly of the endoscope. At a proximal end to be connected to an endoscopic terminal processor which contains an illumination light source along with a video signal processor, the universal cable is provided with a light connector and an electrical connector to couple the illumination light guide and the signal cable with the illumination light source and the video signal processor on the side of the terminal processor.

More particularly, the endoscopic terminal processor usually contains within its casing at least an illumination lamp unit, a video signal processing circuit board, a power supply unit, a transformer and an air pump for sending air or water into a body cavity through the endoscopic insertion instrument. The terminal processor is provided with light and electrical coupling portions on its front side to be coupled with the light and electrical connectors on the universal cable from the endoscope.

In this connection, of the various components which are mounted within the casing of the endoscopic terminal processor, the illumination lamp unit is usually composed of an illumination lamp, a condensing lens, a stop and a filter. The illumination lamp which is normally constituted by a high intensity lamp has a relatively short service life. Therefore, in order to facilitate replacement of the illumination lamp which takes place frequently, normally a couple of lamps are set on a lamp holder plate and, when one of the illumination lamp blows off, the other spare lamp is turned or slid into a light path leading to the light or optical coupling portion. For this reason, the illumination lamp unit is relatively large in size. Besides, it is usually the case that the illumination lamp unit, power supply unit, transformer and air pump are all fixedly mounted at the bottom of the terminal processor casing.

An endoscopic terminal processor of this sort is usually installed in an examination room of a hospital or clinic along with other diagnostic or therapeutic instruments or machines. Therefore, it is desirable for the endoscopic terminal processor to be as compact in size as possible. Since the illumination lamp unit is the largest one in size among the various components and circuit boards which are accommodated within the casing of the terminal processor, its mounting position is usually restricted to a considerable degree in relation with the position of the light coupling portion. Accordingly, various attempts have been made to make the terminal processor compact by appropriating locations of other components and circuit boards to this end. In this regard, it is important to take note of the fact that, as compared with other components and circuit boards, the video signal processing circuit board has a conspicuously broad surface area because of the necessity for mounting a large number of electronic parts including integrated circuits and so on, but is relatively small in thickness. Therefore, the compactness of the terminal processor as a whole depends on how the video processing circuit board is mounted within its casing.

In this regard, for example, it is conceivable to divide the video signal processor circuit board into a plural number of stackable circuit boards of smaller sizes which can be mounted compactly in a narrow space. However, the use of such stackable circuit boards could result in complication of wiring pattern and of connections between the individual boards. Since most of component parts of the endoscopic terminal processor are fixedly mounted on a bottom panel of the casing, it may occur to utilize an upper free space of the casing for mounting a video processing circuit board. In such a case, however, it may become necessary to form the video processor circuit board in a complicate shape other than a simple rectangular shape to evade other component parts which differ largely in height from each other, standing to different heights from the bottom panel of the casing. Therefore, this approach will invite a substantial increase in production cost of the circuit board due to complications of the production process.

If the component parts of the terminal processor are arranged in right and left groups which are located on the right and left sides of a center line of the terminal processor casing, a space of a certain width can be opened up centrally of the casing along the entire length thereof. In such a case, a rectangular video processor circuit board with a broad surfaces area can be compactly accommodated in that narrow space by mounting same in a vertical or upright position instead of in an ordinary horizontal position. In case a video signal processor circuit board is mounted vertically within an endoscopic terminal processor casing, it has to be fixedly supported on either top, side or bottom panel of the casing. However, if the video signal processor circuit board is fixed to only one wall of the casing, it can be destabilized when vibrating movement is transmitted thereto. In order to prevent this, in addition to one of side panels of the casing, the circuit board should be fixed at least to the bottom panel and/or the other side panel of the casing.

Besides the demands for compactness and downsizing, endoscopic terminal processors are required to have a lightweight structure. For this purpose, endoscopic terminal processor are usually reduced in thickness of side, top and bottom walls, and therefore are very susceptible to deformations when an impact is applied thereto, for example, by collisional contact with other object. When an impact is applied on one side of a terminal processor casing, for example, the applied force can be transmitted directly to a video processor circuit board in the casing to cause deformations, disconnections or other damages to the circuit board.

SUMMARY OF THE INVENTION

In view of the foregoing situations, it is an object of the present invention to provide an endoscopic terminal processor of the sort which accommodates within its casing an illumination light source along with a video signal processor for an electronic endoscope, supporting a video processing circuit board of the video processor within the casing vertically in a compact form and securely in a stabilized state against external forces which might otherwise cause deformation or damage to the circuit board or its support member.

In accordance with the present invention, the above-stated objective is achieved by the provision of an endoscopic terminal processor, which comprises: a casing accommodating therein an illumination light source along with a video signal processor for an electronic endoscope, and having optical and electrical coupling portions thereon, the illumination light source including an illumination lamp unit to be optically connected to an illumination light guide from the endoscope through the optical coupling portion for transmission of illumination light, and the video signal processor including a video signal processing circuit board to be connected with a signal cable from the endoscope through the electrical coupling portion; the video signal processing circuit board being supported in an upright position within the casing, and being fixedly connected at one end thereof to a side panel of the casing and loosely supported at the other free end on a damper member adapted to restrict flapping movements of the circuit board about the fixed end.

In a preferred form of the present invention, the damper member is fixed on a bottom surface of the casing, and provided with a pair of gripping plate portions adapted to hold a lower edge portion of the circuit board from opposite sides. Desirably, a noise shielding perforated structure is fitted on and around the circuit board. In some cases, the video signal processing circuit board is composed of a couple of circuit boards, i.e., a circuit board of the patient's side and a circuit board of the secondary side. In such a case, one end of the circuit board of the patient's side is fixed to an inner surface of an end panel of the casing, while one end of the circuit board of the secondary side is fixed to an inner surface of the opposite end panel of the casing. Each one of the other free ends of the two circuit boards is supported loosely on a damper member, and an isolation means is interposed between the two circuit boards to permit signal transmission there between in an electrically isolated state.

The above and other objects, features and advantages of the present invention will become apparent from the following particular description of preferred embodiments, taken in conjunction with the accompanying drawings.

DESCRIPTION OF PREFERRED EMBODIMENTS

Figure 1:
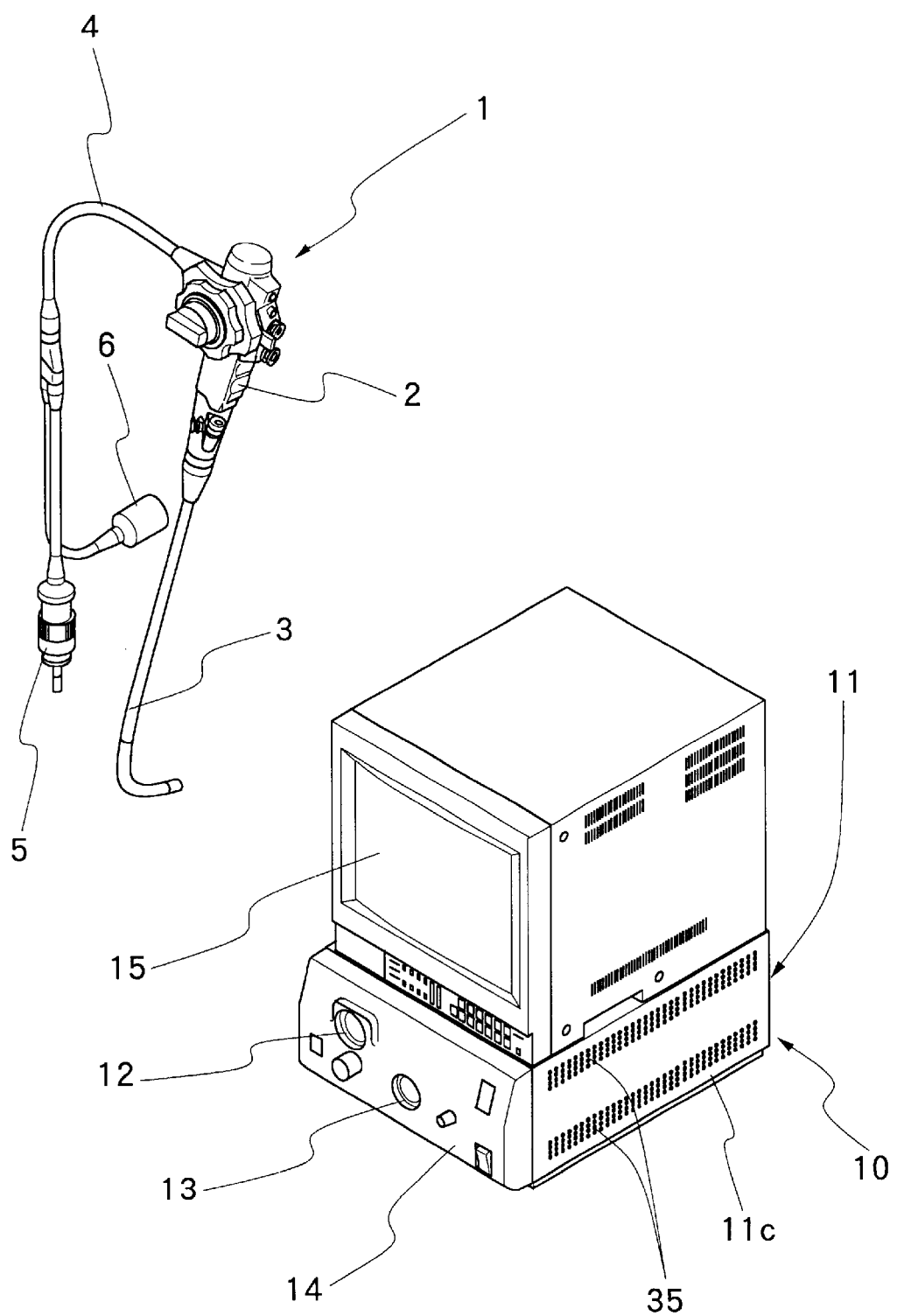
FIG. 1 is a schematic illustration of the general arrangements of an endoscopic examination system for use with an electronic endoscope.

Hereafter, the present invention is described more particularly by way of its preferred embodiments with reference to the accompanying drawings. Referring first to FIG. 1, there is shown an endoscopic examination system for electronic endoscope, which is largely constituted by an electronic endoscope 1 and a terminal processor unit 10 which accommodates within its casing a light source and a video signal processor for the electronic endoscope 1. As seen in that figure, the electronic endoscope 1 is composed of a manipulating head assembly 2, an insertion instrument 3 which is extended out on the front side of the manipulating head 2 for insertion into a body cavity of a patient, and a universal cable 4 which is led out on the rear side of the manipulating head 2. At a proximal end, the universal cable 4 is provided with a light connector 5 and an electrical connector 6 which are disconnectibly connected with the endoscopic terminal processor 10.

By way of the light connector 5, a light guide which is passed through the electronic endoscope 1 is connected to a light source within the terminal processor 10. On the other hand, by way of the electrical connector 6, an electric cable from an image pickup means of the endoscope 1 is connected to a video signal processing circuit within the terminal processor 10. Component parts of the terminal processor 10, including the light source and the video signal processor, are housed in a closed casing 11 which is provided with an optical coupling portion or socket 12 and an electrical coupling portion or socket 13 in its front cover 14 for coupling engagement with the light connector 5 and the electrical connector 6, respectively. Provided on top of the casing 11 is a monitor screen 15 to display endoscopically picked-up images.

Figure 2:
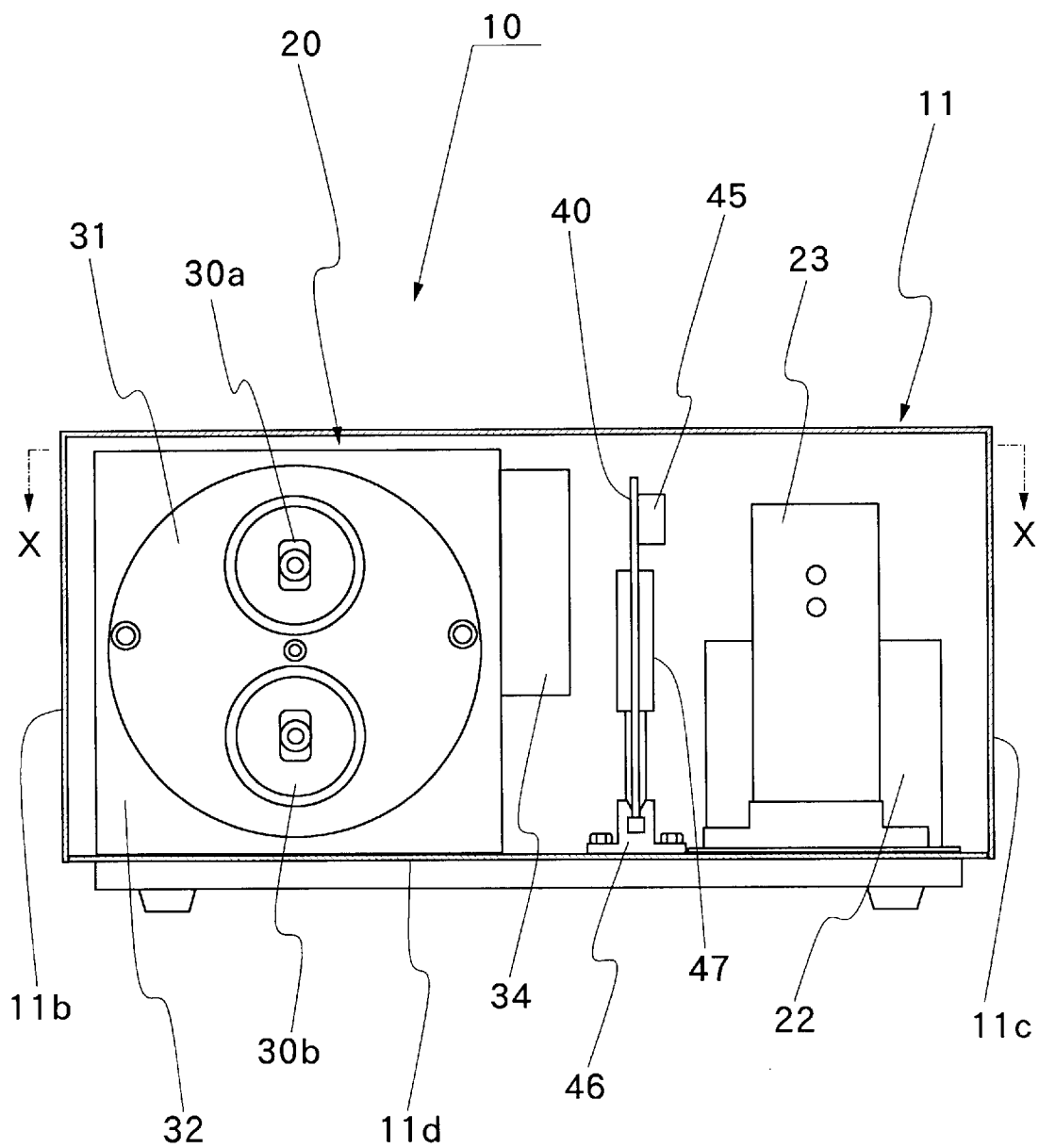
FIG. 2 is a schematic vertical sectional view of a terminal processor of the endoscopic examination system according to one embodiment of the present invention.
Figure 3:
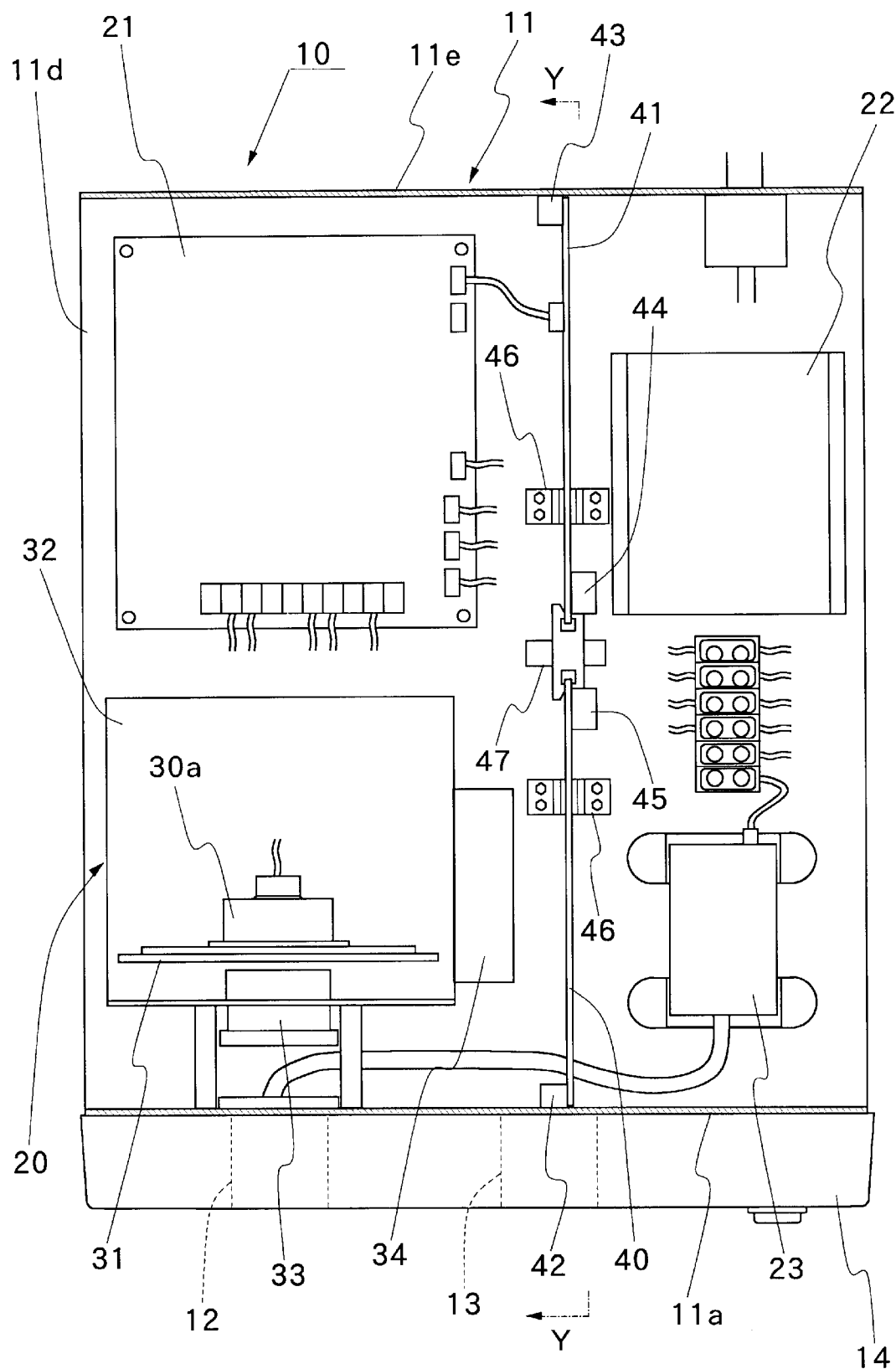
FIG. 3 is a schematic sectional view taken on line X—X of FIG. 2.
Figure 4:
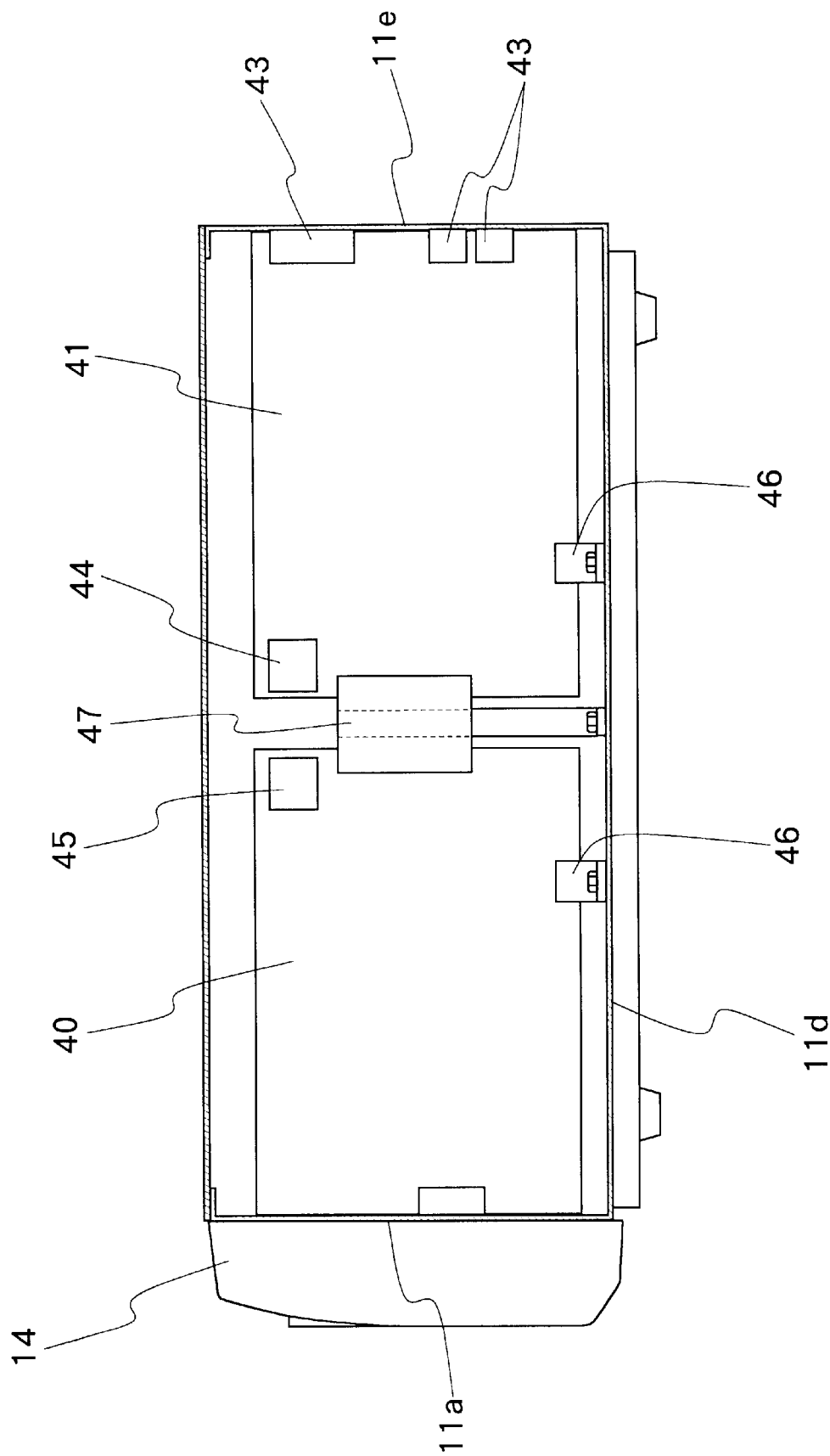
FIG. 4 is a schematic sectional view taken on line Y—Y of FIG. 3.

Shown in FIGS. 2 to 4 are internal arrangements of the terminal processor casing 11. In these figures, indicated at 20 is an illumination lamp unit, at 21 is a power supply unit, at 22 is a transformer, and at 23 is an air pump. The illumination lamp unit 20 is provided with a rotary support plate 31 within a lamp house 32 to support thereon a couple of lamps 30a and 30b. A condensing lens unit 33 is located on the front side of the lamp 30a within the lamp house 32, which is located in a light path toward the optical coupling portion 12. Although not shown in the drawings, the illumination lamp unit 20 further includes a light volume adjuster and a filter if necessary. In the particular example shown, the other lamp 30b is a spare lamp. Further, a cooling fan 34 is fitted in a side panel of the lamp house 32. Left and right side panels 11b and 11c of the lamp house are provided with punched ventilation apertures 35. Thus, upon actuating the fan 34, cooling air is urged to flow into the lamp house through one side panel and flow out through the other side panel, along air flow passages which are formed through the side panels 11b and 11c. The power supply unit 21 is located rearward of the illumination lamp unit 20. With a predetermined spacing in the transverse direction from the illumination lamp unit 20 and power supply unit 21 which are arranged in a row, the air pump 23 and transformer 22 are located in fore and rear positions similarly in a row.

As described above, within the casing 11 of the terminal processor, the illumination lamp unit 20 and power supply unit 21 are fixedly mounted in positions on the side of the left-hand side panel 11b while the air pump 23 and transformer 22 are fixedly mounted in positions on the side of the right-hand side panel 11c, leaving there between a space which is relatively narrow in width but extends substantially over the entire length of the casing. This intermediate space is utilized to accommodate circuit boards 40 and 41 of a video signal processor. Although omitted in the drawings, integrated circuits and a large number of electronic parts are provided or mounted on each one of the circuit boards 40 and 41 of the video signal processor.

Figure 5:
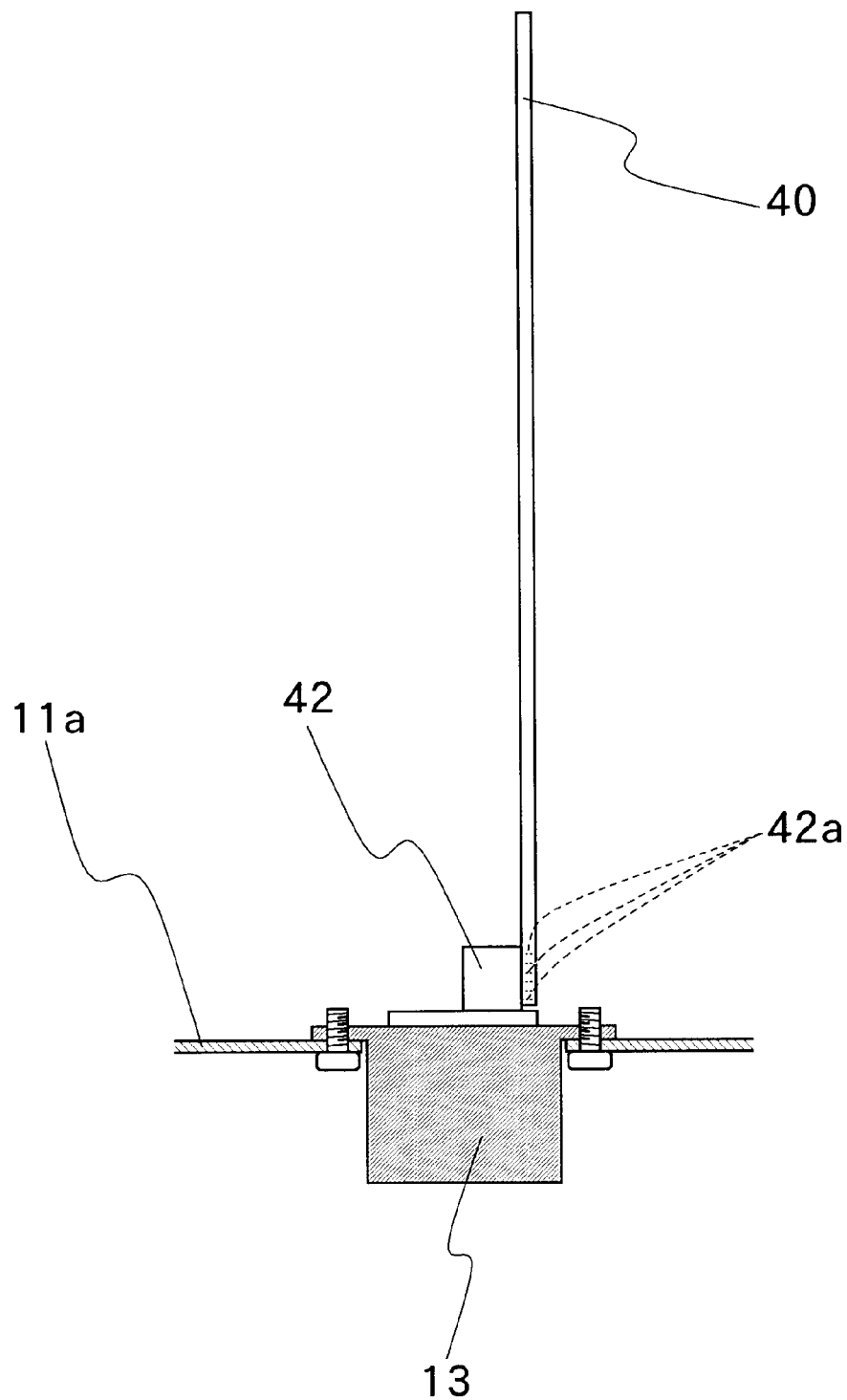
FIG. 5 is a schematic view of a fixed support structure which fixedly supports one end of a first circuit board.
Figure 6:
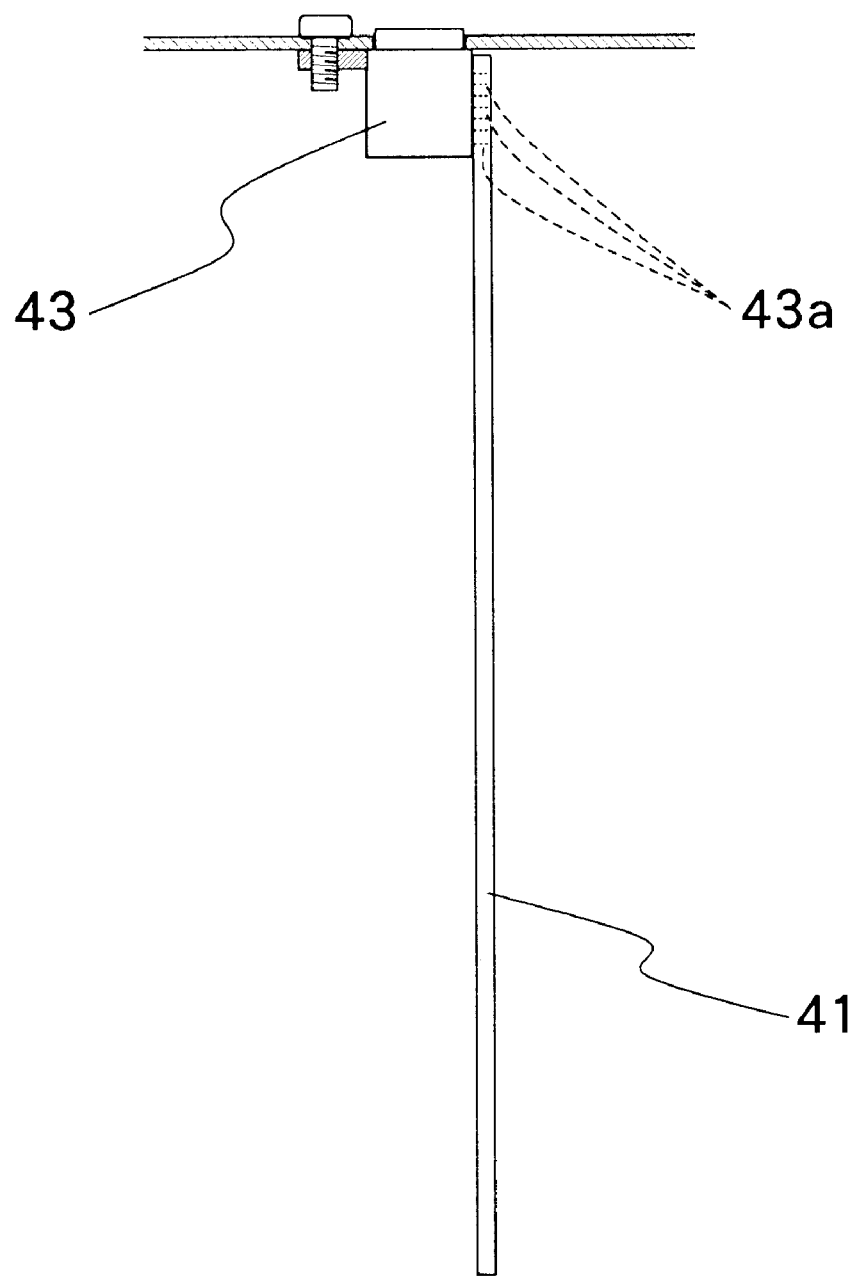
FIG. 6 is a schematic view of a fixed support structure which fixedly supports one end of the other or second circuit board.

In the particular embodiment shown, the video signal processor is divided into a couple of circuit boards 40 and 41, namely, into a circuit board on the patient side and a circuit board on a secondary side which are held in an electrically insulated state from each other. The circuit board 40 is a circuit board on the patient side, which is connected directly with the electrical coupling portion 13. On the other hand, the circuit board 41 is a circuit board on the secondary side, which is connected with the power supply unit 21. As shown in FIGS. 5 and 6, connectors 42 and 43 are attached to the front and rear panels 11a and 11e, respectively, in order to retain these circuit boards 40 and 41 fixedly in position. More particularly, the circuit boards 40 and 41 are engaged with a large number of pins 42a and 43a which are provided on the connectors 42 and 43, and thereby retained fixedly in position. The connector 43 on the side of the rear panel 11e functions to fix the circuit board 41 in position, while the other connector 42 on the side of the front panel 11a also functions as a signal transfer line which electrically connects the circuit board 40 with the electrical coupling portion 13. Further, an optical coupler, including a light-emitting element 44 and a light-receiving element 45, is provided between the circuit board 40 and the other circuit board 41 for isolated signal transmission and reception there between.

The circuit boards 40 and 41 are fixed in the respective positions by insertion of the pins 42a and 43a of the connectors 42 and 43, respectively. These connectors 42 and 43 are connected to one longitudinal end of the circuit board 40 or 41. Therefore, if the other longitudinal end of each one of the circuit boards 40 and 41 is left completely in a free state, the circuit board can be shaken up and down to a considerable degree by rocking movements about the connector 42 or 43 when vibration is applied, resulting in bending deformations or breakage of the connector pins. However, in case other sides of the circuit boards 40 and 41 are fixed completely, the circuit board itself can be deformed or damaged when the casing 11 is subjected to an external compressive force. In order to prevent damages of this sort, the circuit boards 40 and 41 are supported by damper members 46 and 47 which suppresses vibrational movements of the circuit boards 40 and 41 but permits movements in compressive and tensile directions.

Figure 7:
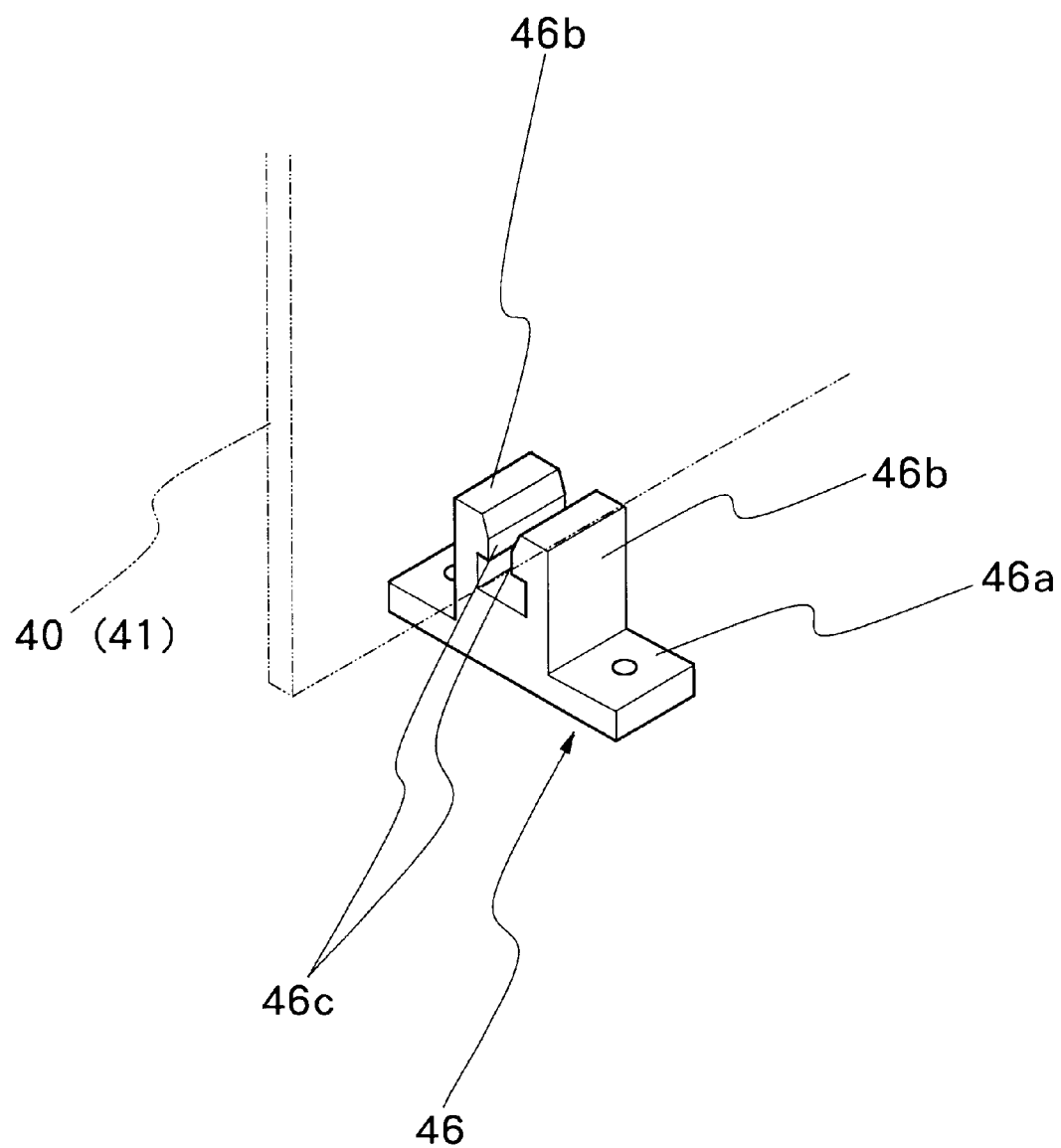
FIG. 7 is a schematic outer view of a first damper member.

As shown in FIG. 7, the damper members 46 are each provided with a pair of board gripping strips 46b which are erected on a base portion 46a. The gripping strips 46b are formed with gripping projections 46c opposingly on the respective inner surfaces which face toward each other. The gripping projections 46b are spaced apart by a gap of a width which is substantially same as or slightly larger than the thickness of the circuit board 40 or 41. The base portion 46a of the damper member 46 is fixed to the bottom panel 11d of the casing by screws or other suitable fixation means. The gripping projections 46c are adapted to hold lower edge portions of the circuit board 40 or 41. More specifically, when gripped between the gripping projections 46c, the lower end of the circuit board 40 or 41 is located in a position intermediate between the upper and lower ends of the gripping strips 46b.

Figure 8:
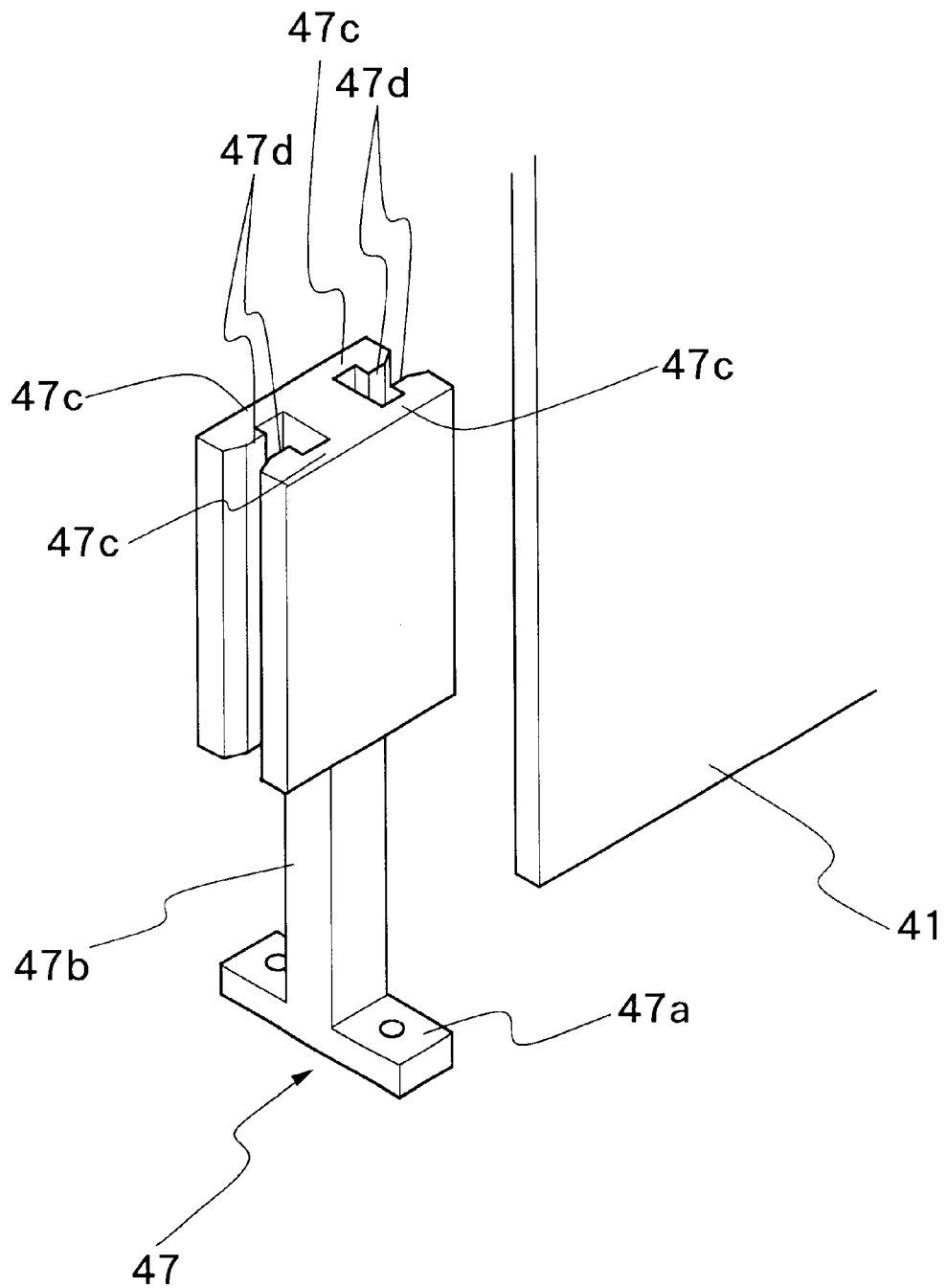
FIG. 8 is a schematic outer view of a second damper member.

On the other hand, the damper member 47 which serves to suppress vibrations of the circuit boards 40 and 41 is adapted to hold inner ends of the circuit boards 40 and 41 on the side away from the outer ends of the circuit boards which are fixedly supported on the connector 42 or 43. For this purpose, as shown in FIG. 8, each one of the damper member 47 is provided with a foot or base portion 47a, a support column 47b which is erected on the base portion 47a, and a pair of gripping portions 47c which are extended laterally from an upper portion of the support column portion 47b and are each provided with gripping projections 47d opposingly across a gap space of a width substantially same as or slightly larger than the thickness of the circuit boards 40 and 41. Inner free ends of the circuit boards 40 and 41 are inserted substantially to a halfway point of the laterally extended gripping portions 47c on the opposite sides of the support column 47b of the damper member 47.

With the arrangements just described, both the circuit board 40 of the patient's side and the circuit board 41 on the secondary side are fixedly supported upright on the connectors 42 and 43. Namely, except the outer ends or side which are fixedly supported on the connectors 42 and 43, the other two sides of the circuit boards 40 and 41 are loosely gripped in the damper members 46 and 47 which restrict flapping movements of the circuit boards but impose no restrictions in particular with regard to movements in other directions. Therefore, even if vibrations is transmitted from the casing 11 to the circuit boards 40 and 41 as would cause the free ends of the circuit boards 40 and 41 to flap to the right and left about the connectors 42 and 43, respectively, the damper members 46 and 47 function to restrict such flapping movements and to retain the circuit boards in a stabilized state. Accordingly, there is no possibility of the connector pins 42a and 43a being forcibly bent by flapping movements of the circuit boards 40 and 41.

With regard to movements of the circuit boards 40 and 41 other than the above-described vibrational movements, collisional impacts or shocks can be transmitted to the circuit boards 40 and 41 when the casing 11 is hit against other objects. On such an occasion, movements in the same direction occur not only to the circuit boards 40 and 41 but also to the connectors 42 and 43 on which the circuit boards 40 and 41 are fixedly supported, and the side panels 11b and 11c to which the connectors 42 and 43 are attached. From the standpoint of protecting the circuit boards 40 and 41 and the connectors 43 and 43 from damages, these movements should be allowed rather than not. Since the damper members 46 and 47 are adapted to permit movements other than the vibrational directions, the circuit boards 40 and 41 as well as the connectors 42 and 43 are protected from direct influences of strong external forces which might be imposed on the casing 11 of the terminal processor 10.

A large number of electronic parts are mounted on each one of the circuit boards 40 and 41. Therefore, it is desirable that both of the circuit boards 40 and 41 can be easily dismantled from the casing for repair or for other purposes. Since the circuit boards 40 and 41 are retained in position simply by the pins 42a and 43a of the connectors 42 and 43, they can be readily removed whenever necessary. As soon as disengaged from the connectors 42 and 43, the circuit boards 40 and 41 can be extracted out of gripping portions 46b and 47c of the damper members 46 and 47 which simply hold the circuit boards 40 and 41 from opposite sides. In order to make the circuit boards 40 and 41 easily separable from the connectors 42 and 43, the width of the gap space between the gripping projections 46c on the gripping portions 46b and 47c of the damper members 46 and 47 is preferred to be slightly larger than the thickness of the circuit boards 40 and 41. Even if the gap space in the gripping portions is widened to some extent, it will not impair the vibration damping functions of the damper members in particular.

Besides, both the circuit boards 40 and 41 are mounted in upright positions within the casing 11 of the terminal processor 10 as described above. This means that the circuit boards 40 and 41 can be accommodated within a narrow space between a right group of component parts including the illumination lamp unit 20 and the power supply unit 21 and a left group including the air pump 23 and the transformer 22. As a consequence, the terminal processor unit 10 can be downsized into a significantly compact form.

Among the various component parts which are built into the casing of the terminal processor 10, the source lamp 30a generates a great deal of heat when lit on. Abnormal temperature elevation within the terminal processor is prevented by cooling air which is taken in through ventilation grills 35 in the side panels 11b and 11c and supplied toward the illumination lamp unit 20 by a fan 34. It may appear that the circuit boards 40 and 41 block circulation of cooling air by the fan 34. However, circulation of cooling air is not blocked because there are wide open spaces on the upper and lower sides of the circuit boards 40 and 41. The circuit boards 40 and 41 also give off heat but are cooled efficiently because they are located in the path of cooling air which is circulated by the fan 34.

Figure 9:
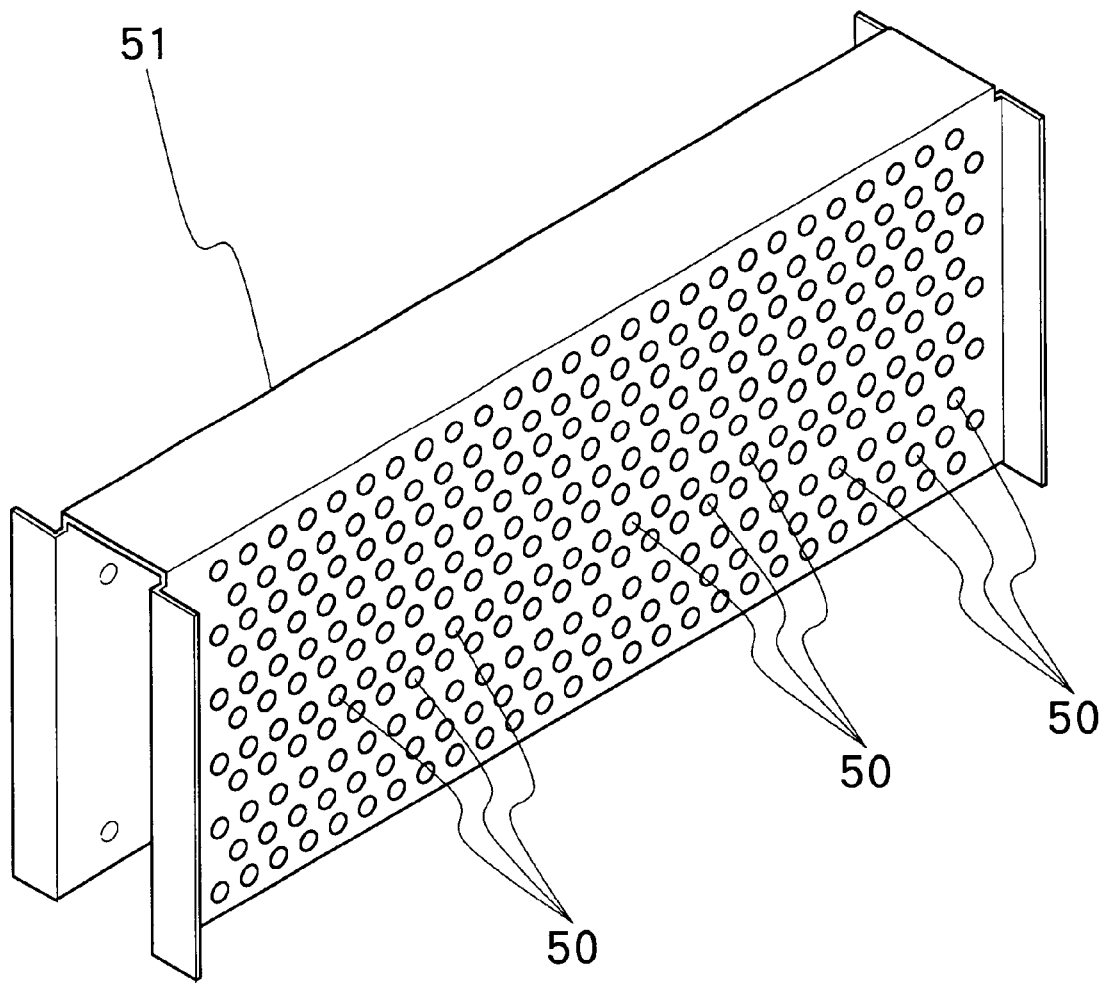
FIG. 9 is a schematic outer view of a noise cut-off member fitted around the circuit board.

Further, a clock signal generator, which is provided on either the circuit board 40 or 41 to supply a clock signal to the video signal processor system as a whole, can be a cause of troubles because clock signals could cause malfunctioning to other electrical instruments or appliances in surrounding areas if released to the outside as a noise. In order to prevent clock signals from going out as a noise, it is preferable to cover the circuit boards 40 and 41 in a noise shield member 51 having a U-shape structure as shown in FIG. 9. The noise shield member 51 is provided with a multitude of punched holes 50 of such a diameter as to form a shielding against noises of the clock signal frequency. Of course, the punched holes in the noise shield member 51 permit circulation of cooling air in and through the casing 11.

Although by way of example a couple of circuit boards 40 and 41 are used in the foregoing embodiment, a single board type processor may be employed in combination with a suitable isolation means. Besides, the connectors 42 and 43 are not necessarily required for fixing the circuit boards 40 and 41 to the side panels 11b and 11c. When connectors are used for this purpose, the number of connectors should be determined according to the weight and size of the circuit boards. Of course, the number of the damper members should be determined similarly according to the weight and size of the circuit boards.

As clear from the foregoing description, according to the present invention, the circuit board or boards of a video signal processor can be accommodated compactly within a casing of an endoscopic terminal processor, and retained in position in a cushioned state, free of deformation or a damage which might otherwise be caused to the circuit boards or to circuit board support portions when a strong external force is applied to the casing.

What is claimed is:

1. An endoscopic terminal processor, comprising:
   a casing accommodating therein an illumination light source along with a video signal processor for an electronic endoscope, and having optical and electrical coupling portions thereon, said illumination light source including an illumination lamp unit to be optically connected to an illumination light guide through said optical coupling portion for transmission of illumination light, and said video signal processor including a video signal processing circuit board to be connected with a signal cable from said endoscope through said electrical coupling portion;
   said video signal processing circuit board being supported in an upright position within said casing, and being fixedly connected at one end thereof to a side panel of said casing;
   a damper member being fixed to a bottom surface of said casing to support opposite sides of said circuit board at the other free end;
   said damper member further comprising:
      a pair of gripping strips having gripping projections opposingly on each inner surface to face toward each other defining a space into which the circuit board is inserted;
      said gripping projections being adapted to restrict flapping movements of said circuit board about said fixed one end but to permit movements in compressive and tensile directions.

2. An endoscopic terminal processor as defined in claim 1, further comprising a cover structure fitted on and around said circuit board and containing a multitude of noise shielding holes.

3. An endoscopic terminal processor as defined in claim 1, wherein said circuit board is composed of a circuit board of a patient's side having one end thereof fixed to an inner surface of an end panel of said casing, and a circuit board of a secondary side having one end thereof fixed to an inner surface of an opposite end panel, the other free end of each one of said circuit boards being supported loosely on a damper member adapted to restrict flapping movement of said circuit board about said fixed end; and
   said terminal processor further comprising an isolation means interposed between said circuit board on a patient's side and said circuit board on the secondary side to permit signal transmission there between in an electrically isolated state.

4. An endoscopic terminal processor, comprising:
   a casing accommodating therein an illumination light source along with a video signal processor for an electronic endoscope, and having optical and electrical coupling portions thereon, said illumination light source including an illumination lamp unit to be optically connected to an illumination light guide through said optical coupling portion for transmission of illumination light, and said video signal processor including a video signal processing circuit board to be connected with a signal cable from said endoscope through said electrical coupling portion;
   said video signal processing circuit board being supported in an upright position within said casing, and being fixedly connected at one end thereof to a side panel of said casing and loosely supported at the other free end on a damper member adapted to restrict flapping movements of said circuit board about said fixed one end, wherein said circuit board is composed of a circuit board of a patient's side having one end thereof fixed to an inner surface of an end panel of said casing, and a circuit board of a secondary side having one end thereof fixed to an inner surface of an opposite end panel, the other free end of each one of said circuit boards being supported loosely on a damper member adapted to restrict flapping movement of said circuit board about said fixed end; and said terminal processor further comprising an isolation means interposed between said circuit board on patient's side and said circuit board on the secondary side to permit signal transmission there between in an electrically isolated state.

* * * * *

UNITED STATES PATENT AND TRADEMARK OFFICE
CERTIFICATE OF CORRECTION

PATENT NO.    : 6,450,947 B1                                    Page 1 of 1
DATED         : September 17, 2002
INVENTOR(S)   : Arai It is certified that error appears in the above-identified patent and that said Letters Patent is hereby corrected as shown below:

<u>Title page,</u>
Item [45], and [*] Notice information should read as follows:

-- [45]  **Date of Patent:  \*Sep. 17, 2002**

[*] Notice:    This patent issued on a continued prosecution application filed under 37 CFR 1.53(d), and is subject to the twenty year patent term provisions of 35 U.S.C. 154(a)(2).

Subject to any disclaimer, the term of this patent is extended of adjusted under 35 U.S.C. 154(b) by 0 days. --

Signed and Sealed this

Eleventh Day of March, 2003

JAMES E. ROGAN
*Director of the United States Patent and Trademark Office*